United States Patent [19]

Everly et al.

[11] 4,456,770
[45] Jun. 26, 1984

[54] CHEMICAL PROCESS FOR PREPARING 1,3 DIKETONES

[75] Inventors: Charles R. Everly; Jerry M. Roper, both of Baton Rouge, La.

[73] Assignee: Ethyl Corportation, Richmond, Va.

[21] Appl. No.: 415,019

[22] Filed: Sep. 7, 1982

[51] Int. Cl.³ ............................................. C07C 45/61
[52] U.S. Cl. .................................... 568/315; 568/308
[58] Field of Search ............................... 568/315, 312

[56] References Cited

U.S. PATENT DOCUMENTS

| | | | |
|---|---|---|---|
| 4,060,556 | 11/1977 | Parker | 568/315 |
| 4,186,151 | 1/1980 | Kubota et al. | 568/315 |
| 4,208,425 | 6/1980 | Diana | 568/315 |

*Primary Examiner*—James H. Reamer
*Attorney, Agent, or Firm*—Donald L. Johnson; John F. Sieberth; Willard G. Montgomery

[57] ABSTRACT

Novel (3',5'-dihydrocarbyl-4'-hydroxybenzyl)-1,3-diketones are prepared by reacting an N,N-dihydrocarbyl-2,6-dihydrocarbyl-4-aminomethylphenol with a 1,3-diketone in the presence of a basic substance. The products are useful as antioxidants.

30 Claims, No Drawings

CHEMICAL PROCESS FOR PREPARING 1,3 DIKETONES

CROSS-REFERENCE TO RELATED APPLICATION

This application is related to our co-pending U.S. application, Ser. No. 415,020, entitled CHEMICAL PROCESS, filed contemporaneously herewith on Sept. 7, 1982, directed to the preparation of novel (3',5'-dihydrocarbyl-4'-hydroxybenzyl)-1,3-diketones by reacting an N,N-dihydrocarbyl-2,6-dihydrocarbyl-4-aminomethylphenol with a 1,3-diketone and an alkyl halide in the presence of an alkali or an alkaline earth metal hydride. These novel compounds are useful as antioxidants for gasoline, engine and industrial oils, plastics and rubber.

TECHNICAL FIELD

This invention relates to novel an eminently useful (3',5'-dihydrocarbyl-4'-hydroxybenzyl)-1,3-diketones and the preparation and uses thereof as antioxidants for oxidizable organic materials when such materials are exposed to oxidative degradative conditions.

THE INVENTION

The materials of the invention are prepared by reacting an N,N-dihydrocarbyl-2,6-dihydrocarbyl-4-aminomethylphenol with a 1,3-diketone and a basic material, preferably selected from alkali metal hydroxides, alkali metal salts of a weak acid, alkaline earth metal hydroxides, alkaline earth metal salts of a weak acid, amine bases and mixtures of the same.

Thus, in one embodiment of the invention there is provided a novel process for the preparation of (3',5'-dihydrocarbyl-4'-hydroxybenzyl)-1,3-diketones which comprises reacting an N,N-dihydrocarbyl-2,6-dihydrocarbyl-4-aminomethylphenol with a 1,3-diketone and a basic substance.

In another embodiment of the invention, there is provided a novel process for the preparation of (3',5'-dihydrocarbyl-4'-hydroxybenzyl)-1,3-diketones which comprises reacting an N,N-dihydrocarbyl-2,6-dihydrocarbyl-4-aminomethylphenol with a 1,3-diketone and a basic material selected from the group consisting of alkali metal hydroxides, alkali metal salts of a weak acid, alkaline earth metal hydroxides, alkaline earth metal salts of a weak acid, amine bases and mixtures of the same.

The process can be illustrated schematically by the following equations. Compounds having the general formula

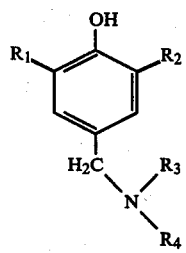

(I)

are reacted with compounds having the general formula

$R_5COCH_2COR_6$ (II)

in the presence of a basic material as described above to yield a benzylated 1,3-diketone having the structural formula

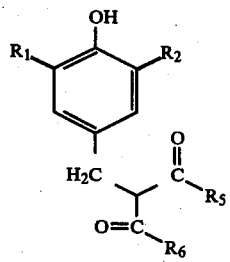

(III)

In the structural formulas above $R_1$ and $R_2$ are the same or different and are hydrogen or hydrocarbyl radicals, preferably alkyl, aralkyl or cycloalkyl radicals having up to at least 40 carbon atoms, and preferably from 3 to 8 atoms, at least one of which is branched on the alpha-carbon atom, with the provision that at least one of $R_1$ or $R_2$ must be other than hydrogen; $R_3$ and $R_4$ are the same or different and are linear, branched or unbranched, alkyl, aralkyl or cycloalkyl radicals having up to at least 20 carbon atoms, and $R_5$ and $R_6$ are the same or different and can be linear or branched alkyl radicals having up to at least 20 carbon atoms.

Thus, in another embodiment of the present invention there is provided a process for the preparation of (3',5'-dihydrocarbyl-4'-hydroxybenzyl)-1,3-diketones having the general formula

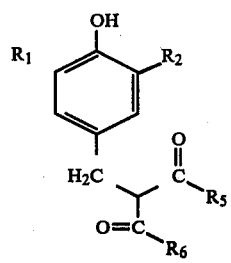

(III)

which comprises reacting an N,N-dihydrocarbyl-2,6-dihydrocarbyl-4-aminomethylphenol of the general formula

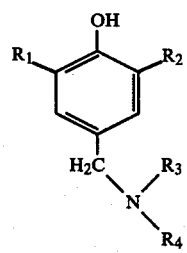

(I)

with a 1,3-diketone of the general formula

$R_5COCH_2COR_6$ (II)

in the presence of a basic substance wherein in the structural formulas above $R_1$ and $R_2$ are the same or different and are hydrogen or hydrocarbyl radicals having up to at least 40 carbon atoms with the provision that at least one of $R_1$ or $R_2$ must be other than hydrogen; $R_3$ and $R_4$ are the same or different and are linear, branched or unbranched alkyl, aralkyl or cycloalkyl radicals having up to at least 20 carbon atoms, and $R_5$ and $R_6$ are the same or different and are linear or branched alkyl radicals having up to at least 20 carbon atoms.

Representative examples of radicals described above are secondary radicals such as secondary butyl, secondary amyl, secondary octyl; tertiary radicals such as tertiary butyl, tertiary hexyl and tertiary decyl; alkyl radicals such as methyl, ethyl, propyl, butyl, nonyl, decyl, tetradecyl, hexadecyl, nonadecyl; aralkyl radicals such as methyl phenyl and pentyl phenyl, and cycloalkyl radicals such as cyclopentyl, cyclohexyl and cycloheptyl radicals.

Representative examples of the Group I compounds are
N,N-dimethyl,2,6-di-t-butyl-4-aminomethylphenol,
N,N-dimethyl,2-methyl-6-isopropyl-4-aminomethylphenol,
N,N-dimethyl,2-methyl-6-t-butyl-4-aminomethylphenol,
N,N-dimethyl,2,6-diisopropyl-4-aminomethylphenol,
N,N-dimethyl,2-sec-butyl-4-aminomethylphenol,
N,N-dimethyl,2-isopropyl-4-aminomethylphenol,
N,N-dimethyl,2-t-butyl-4-aminomethylphenol,
N,N-diethyl,2,6-t-butyl-4-aminomethylphenol,
N,N-dioctyl,2,6-di-t-butyl-4-aminomethylphenol,
N,N-dioctyl,2-ethyl-6-t-butyl-4-aminomethylphenol,
N,N-dioctyl,2,6-diheptyl-4-aminomethylphenol,
N,N-dioctyl,2-ethyl-6-methyl-4-aminomethylphenol,
N,N-dioctyl,2-t-butyl-6-heptyl-4-aminomethylphenol,
N-ethyl,N-methyl,2,6-di-t-butyl-4-aminomethylphenol,
N-octyl,N-methyl,2-methyl-6-ethyl-4-aminomethylphenol,
3,5-di-t-butyl-4-hydroxybenzylpiperidine,
3,5-di-t-butyl-4-hydroxybenzylmorpholine, and
3,5-di-t-butyl-4-hydroxybenzylpyrrolidine.

Representative examples of Group II 1,3-dicarbonyl compounds are
2,4-pentanedione,
2,4-heptanedione,
4,6-nonanedione,
2,6-dimethyl-3,5-heptanedione,
1-hexyl-1,3-butanedione,
1-hexyl-2,4-pentanedione, and
1,3-dihexyl-1,3-propanedione.

Representative examples of Group III benzylated 1,3-diketone compounds, functioning as antioxidants, are
3-(3',5'-di-t-butyl-4'-hydroxybenzyl)-2,4-pentanedione,
3-(3'-methyl-5'-isopropyl-4'-hydroxybenzyl)-2,4-pentanedione,
3-(3'-methyl-5'-t-butyl-4'-hydroxybenzyl)-2,4-pentanedione,
3-(3',5'-diisopropyl-4'-hydroxybenzyl)-2,4-pentanedione,
3-(3'-sec-butyl-4'-hydroxybenzyl)-2,4-pentanedione,
3-(3'-isopropyl-4'-hydroxybenzyl)-2,4-pentanedione,
3-(3'-t-butyl-4'-hydroxybenzyl)-2,4-pentanedione,
3-(3'-ethyl-5'-methyl-4'-hydroxybenzyl)-2,4-heptanedione,
5-(3',5'-dioctyl-4'-hydroxybenzyl)-4,6-nonanedione,
4-(3'-t-butyl-5'-heptyl-4'-hydroxybenzyl)-2,6-dimethyl-3,5-heptanedione,
2-(3',5'-dioctyl-4'-hydroxybenzyl)-1-hexyl-1,3-butanedione,
3-(3',5'-dioctyl-4'-hydroxybenzyl)-1-hexyl-2,4-pentanedione, and
2-(3',5'-dioctyl-4'-hydroxybenzyl)-1,3-dihexyl-1,3-propanedione.

In general, the basic reactant of the instant process may be any of the alkali metal or alkaline earth metal hydroxides, alkali metal or alkaline earth metal salts of a weak acid, amine bases or mixtures of the same. These include sodium hydroxide, potassium hydroxide, barium hydroxide, rubidium hydroxide, cesium hydroxide, sodium carbonate, potassium carbonate, cesium carbonate, rubidium carbonate, potassium sulfite, sodium borate, potassium acetate, diazabicyclononane, pyridine, tetramethylguanidine and 1,4-diazabicyclo(2,2,2)-octane, and the like.

The process of the invention is carried out by reacting the benzylamine starting material with at least 1 molar equivalent of β-diketone reactant and 1 molar equivalent of base although an excess of either or both diketone and basic reactant can be used. A preferred range of β-diketone reactant to benzylamine reactant is from about 1 to 10 moles of β-diketone per mole of benzylamine. A preferred range of basic reactant to benzylamine reactant ranges from about 1 to 10 moles of base per mole of benzylamine. It should be stated, however, that the use of increasing amounts of basic material in the process tends to decrease the yield of desired benzylated 1,3-diketone product.

The reaction is advantageously conducted at a temperature of from about 50° C. to about 500° C. While lower temperatures can be used, the reaction rates are generally correspondingly lower. Temperatures above 500° C. can be used, but excessive decomposition of the reaction components can occur. Reflux temperature at atmospheric pressure is effective and preferred.

Typically, the reaction can be conducted at atmospheric pressure. However, higher pressures up to about 1000 psig may be used, if desired.

The use of a solvent for the reaction mixture is not generally required, especially if an excess of 1,3-dicarbonyl reactant is used. However, if desired, a solvent which is inert under the reaction conditions, i.e., those solvents which do not enter into the reaction, may be added to the reaction vessel. Useful solvents comprise aprotic solvents which include ethers such as diethyl ether, dibutyl ether, 1-ethoxyhexane, tetrahydrofuran, 1,4-dioxane, 1,3-dioxolane, diglyme, 1,2-diethoxyethane, and tertiary amines such as pyridine, N-ethylpiperidine, triethylamine, tributylamine, N,N-diphenyl-N-methylamine, N,N-dimethylalanine, etc. Especially useful solvents are dipolar aprotic solvents such as dimethyl sulfoxide, N,N-dimethylformamide, N,N-dimethylacetamide, dimethyl sulfone, tetramethylene sulfone, N-methylpyrrolidinone, acetonitrile and like materials. Other solvents which are inert under the reaction conditions may be used: for example, low boiling hydrocarbons, halogenated hydrocarbons, examples of which are benzene, toluene, tetrachloroethane, the chlorinated benzenes, the chlorinated toluenes, etc. and lower alkanols having up to about 6 carbon atoms. These include, methanol, ethanol, n-propanol, isopropyl alcohol, n-butanol, sec-butyl alcohol, t-butyl alcohol, n-pentanol, isopentyl alcohol, n-hexanol and isohexyl alcohol.

The amount of solvent can be expressed as a volume ratio of solvent to benzylamine reactant. Suitable volume ratios of solvent to benzylamine reactant can be from about 0/1 to about 500/1 and preferably from about 1/1 to about 300/1.

The mode of addition in the process is not particularly critical. Accordingly, it is convenient to add the benzylamine reactant to a mixture of the other materials, add the 1,3-dicarbonyl compound to a mixture of the other materials, add the basic reactant to a mixture of the other materials, add the reactants to a mixture of the benzylamine and solvent, introduce all ingredients simultaneously into the reaction zone, or the like.

The process should be carried out for the time sufficient to convert substantially all of the benzylamine reactant to the corresponding benzylated 1,3-diketone. The length of time for optimum yield will depend primarily upon the reaction temperature and the particular solvent, if any, used in the reaction. In general, excellent yields of the benzylated 1,3-diketones are obtained in from about two to twenty-four hours.

Although not required, the process can be conducted in a substantially anhydrous reaction system, and accordingly, the components of the reaction system are brought together and maintained under a substantially dry, inert atmosphere. By "substantially anhydrous" is meant a reaction system wherein the total amount of water present is no more than about 5 percent by weight, based on the reaction mixture. When the amount of water in the system exceeds this, both reaction rate and yield of product decrease.

The process may readily be conducted in a batchwise, semibatch or continuous manner and in conventional equipment.

The process of the invention when run continuously can be illustrated schematically by the equation shown below. $R_1$, $R_2$, $R_3$, $R_4$, $R_5$ and $R_6$ are the same radicals as described and exemplified above.

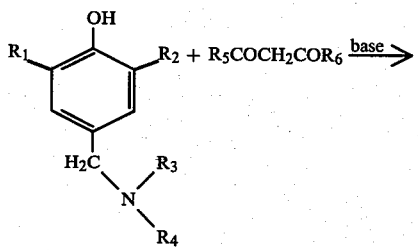

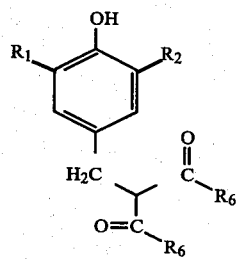

Under the reaction conditions, the benzylamine reactant is alkylated to initially yield a quaternary ammonium salt of the benzylamine which subsequently eliminates a tertiary amine component from the salt to produce a quinone methide intermediate which undergoes nucleophilic attack by the 1,3-diketone reactant to form the desired benzylated 1,3-diketone product. During the course of the reaction some bis(hydroxyphenyl)methane by-product and a 4-(3-oxobutyl)phenol moiety can be formed.

The benzylated 1,3-diketone product is easily separated from the reaction mixture by such means as distillation, extraction, crystallization and other methods obvious to those skilled in the chemical processing art.

The benzylated 1,3-diketone products prepared by the process of this invention have antioxidant properties and are capable of stabilizing polymers normally subject to oxidative degradation when incorporated into the polymers using conventional techniques such as by addition to polymer lattices; or by addition to solid polymers on a mill or in a Banbury. Further, the novel compounds of this invention are effective antioxidants in both unleaded and leaded gasolines made from a wide variety of base stocks and for engine and industrial oils which are derived from crude petroleum or produced synthetically.

The practice of this invention will be still further apparent by the following illustrative examples.

Example I

A mixture of N,N-dimethyl-2,6-di-t-butyl-4-aminomethylphenol (2.63 g, 10 mmols), sodium hydroxide (0.6 g, 15 mmols) and acetylacetone (24 mmols, 10% solution) was refluxed for 3 hours in a glass reaction vessel. Acetylacetone was distilled under reduced pressure to afford an oily residue containing 3-(3',5'-di-t-butyl-4'-hydroxyphenyl)-2,4-pentanedione (80% by VPC). Crystallization from ethanol:water afforded a single crop of 3-(3',5'-di-t-butyl-4'-hydroxyphenyl)-2,4-pentanedione (65%, overall yield, 97% pure).

Example II

A mixture of the N,N-dimethyl-2,6-di-t-butyl-4-aminomethylphenol (10.5 g, 40 mmols), sodium hydroxide (1.8 g, 45 mmols) and acetylacetone (24 mLs, 10% solution) was refluxed for 3 hours. Acetylacetone was distilled under reduced pressure to afford an oily residue of the 3-(3',5'-di-t-butyl-4'-hydroxyphenyl)-2,4-pentanedione compound (97% by VPC).

Example III

A mixture of the N,N-dimethyl-2,6-di-t-butyl-4-aminomethylphenol (10.5 g, 40 mmols), sodium hydroxide (3.6 g, 90 mmols) and acetylacetone (24 mLs, 10% solution) was refluxed for 3 hours. Acetylacetone was distilld under reduced pressure to afford an oily residue of the 3-(3',5'-di-t-butyl-4'-hydroxyphenyl)-2,4-pentanedione compound (37% by VPC).

Having disclosed the process of the present invention, one skilled in the art can readily envision various modifications and changes which are nevertheless within the scope of the invention. Therefore, it is desired that the process of this invention be limited only by the lawful scope of the appended claims.

We claim:

1. A process for the preparation of a compound having the general structural formula

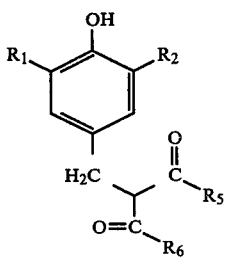

which comprises reacting a compound of the general structural formula

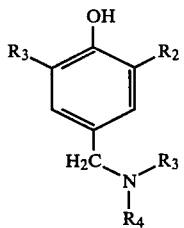

with a 1,3-diketone of the general structural formula $R_5COCH_2COR_6$ (II)

in the presence of a basic substance, which is an alkali metal hydroxide, an alkali metal salt of a weak acid, an alkaline earth metal hydroxide, an alkaline earth metal salt of a weak acid, amine bases or mixtures of the same, wherein $R_1$ and $R_2$ are the same or different and are hydrogen or hydrocarbyl radicals having up to at least 40 carbon atoms with the provision that at least one of $R_1$ or $R_2$ must be other than hydrogen, $R_3$ and $R_4$ are the same or different and are linear, branched or unbranched alkyl, aralkyl or cycloalkyl radicals having up to at least 20 carbon atoms, or $R_3$ and $R_4$ taken together form a piperidine, morpholine, or pyrrolidine ring, and $R_5$ and $R_6$ are the same or different and are linear or branched alkyl radicals having up to at least 20 carbon atoms.

2. The process of claim 1 wherein compounds having the general structural formula (I) are selected from the group consisting of N,N-dimethyl,2,6-di-t-butyl-4-aminomethylphenol, N,N-dimethyl,2-methyl-6-isopropyl-4-aminomethylphenol, N,N-dimethyl,2-methyl-6-t-butyl-4-aminomethylphenol, N,N-dimethyl,2,6-diisopropyl-4-aminomethylphenol, N,N-dimethyl,2-sec-butyl-4-aminomethylphenol, N,N-dimethyl,2-isopropyl-4-aminomethylphenol, N,N-dimethyl,2-t-butyl-4-aminomethylphenol, N,N-diethyl,2,6-di-t-butyl-4-aminomethylphenol, N,N-dioctyl,2,6-di-t-butyl-4-aminomethylphenol, N,N-dioctyl,2-ethyl-6-t-butyl-4-aminomethylphenol, N,N-dioctyl,2,6-diheptyl-4-aminomethylphenol, N,N-dioctyl,2-ethyl-6-methyl-4-aminomethylphenol, N,N-di-octyl,2-t-butyl-6-heptyl-4-aminomethylphenol, N-ethyl,N-methyl-2,6-di-t-butyl-4-aminomethylphenol, N-octyl,N-methyl,2-methyl-6-ethyl-4-aminomethylphenol, 3,5-di-t-butyl-4-hydroxybenzylpiperidine, 3,5-di-t-butyl-4-hydroxybenzylmorpholine, and 3,5-di-t-butyl-4-hydroxybenzylpyrrolidine.

3. The process of claim 1 wherein compounds having the general structural formula (II) are selected from the group consisting of 2,4-pentanedione, 2,4-heptanedione, 4,6-nonanedione, 2,6-dimethyl-3,5-heptanedione, 1-hexyl-1,3-butanedione, 1-hexyl-2,4-pentanedione, and 1,3-dihexyl-1,3-propanedione.

4. The process of claim 1 wherein said basic substance is selected from the group consisting of sodium hydroxide, potassium hydroxide, barium hydroxide, rubidium hydroxide, cesium hydroxide, sodium carbonate, potassium carbonate, cesium carbonate, rubidium carbonate, potassum sulfite, sodium borate, potassium acetate, diazabicyclononane, pyridine, tetramethylguanidine and 1,4-diazabicyclo(2,2,2)-octane.

5. The process of claim 1 wherein the compound produced is 3-(3',5'-di-t-butyl-4'-hydroxybenzyl)-2,4-pentanedione.

6. The process of claim 1 wherein the compound produced is 3-(3'-methyl-5'-isopropyl-4'-hydroxybenzyl)-2,4-pentanedione.

7. The process of claim 1 wherein the compound produced is 3-(3'-methyl-5'-t-butyl-4'-hydroxybenzyl)-2,4-pentanedione.

8. The process of claim 1 wherein the compound produced is 3-(3',5'-diisopropyl-4'-hydroxybenzyl)-2,4-pentanedione.

9. The process of claim 1 wherein the compound produced is 3-(3'-sec-butyl-4'hydroxybenzyl)-2,4-pentanedione.

10. The process of claim 1 wherein the compound produced is 3'(3'-isopropyl-4'-hydroxybenzyl)-2,4-pentanedione.

11. The process of claim 1 wherein the compound produced is 3-(3'-t-butyl-4'-hydroxybenzyl)-2,4-pentanedione.

12. The process of claim 1 wherein the compound produced is 3-(3'-ethyl-5'-methyl-4'-hydroxybenzyl)-2,4-heptanedione.

13. The process of claim 1 wherein the compound produced is 5-(3',5'-dioctyl-4'-hydroxybenzyl)-4,6-nonanedione.

14. The process of claim 1 wherein the compound produced is 4-(3'-t-butyl-5'-heptyl-4'-hydroxybenzyl)-2,6-dimethyl-3,5-heptanedione.

15. The process of claim 1 wherein the compound produced is 2-(3',5'-dioctyl-4'-hydroxybenzyl)-1-hexyl-1,3-butanedione.

16. The process of claim 1 wherein the compound produced is 3-(3',5'-dioctyl-4'-hydroxybenzyl)-1-hexyl-2,4-pentanedione.

17. The process of claim 1 wherein the compound produced is 2-(3',5'-dioctyl-4'-hydroxybenzyl)-1,3-dihexyl-1,3-propanedione.

18. The process of claim 1 wherein the molar ratio of 1,3-diketone reactant to benzylamine reactant is from about 1-10 moles of diketone per mole of benzylamine.

19. The process of claim 1 wherein the molar ratio of basic reactant to benzylamine reactant is from about 1-10 moles of basic reactant per mole of benzylamine.

20. The process of claim 1 wherein said reaction is conducted at elevated temperature.

21. The process of claim 20 wherein said reaction is carried out at a temperature of from about 50° C. to about 500° C.

22. The process of claim 1 wherein said reaction is carried out under pressure in the range of from about atmospheric up to about 1000 psig.

23. The process of claim 1 wherein said reaction is carried out at temperature in the range of about 50° C. to about 500° C. and under pressure in the range of about atmospheric to about 1000 psig.

24. The process of claim 1 wherein said reaction is carried out in the presence of a solvent which is inert under the reaction conditions.

25. The process of claim 24 wherein the said solvent is an aprotic solvent.

26. The process of claim 24 wherein said aprotic solvent is a dipolar aprotic solvent.

27. The process of claim 26 wherein said dipolar aprotic solvent is selected from dimethyl sulfoxide, N,N-dimethylformamide, N,N-dimethylacetamide, dimethyl sulfone, tetramethylene sulfone, N-methylpyrrolidinone and acetonitrile.

28. The process of claim 24 wherein said solvent is selected from the group consisting of low boiling hydrocarbons, halogenated hydrocarbons and lower alkanols having up to about 6 carbon atoms.

29. The process of claim 18 wherein the volume ratio of solvent to benzylamine reactant is from about 0/1 to about 500/1.

30. The process of claim 1 wherein the reaction is carried out under a substantially dry inert atmosphere.

* * * * *

UNITED STATES PATENT AND TRADEMARK OFFICE
CERTIFICATE OF CORRECTION

PATENT NO. : 4,456,770
DATED : June 26, 1984
INVENTOR(S) : Charles R. Everly et al.

It is certified that error appears in the above-identified patent and that said Letters Patent is hereby corrected as shown below:

Column 3, line 25, "N,N-diethyl, 2,6-t-butyl" should read -- N,N-diethyl, 2,6-di-t-butyl --;

Column 6, line 35, "hydroxyphenyl" should read -- hydroxybenzyl --;
line 45, "hydroxyphenyl" should read -- hydroxybenzyl --;
line 55, "distilld" should read -- distilled --;
line 56, "hydroxyphenyl" should read -- hydroxybenzyl --;

Column 10, line 7, "18" should read -- 24 --;
line 8, "0/1" should read -- 1/1 --.

Signed and Sealed this

Fifth Day of March 1985

[SEAL]

Attest:

DONALD J. QUIGG

Attesting Officer

Acting Commissioner of Patents and Trademarks